(12) United States Patent
Sellergren et al.

(10) Patent No.: US 7,393,909 B2
(45) Date of Patent: *Jul. 1, 2008

(54) POROUS, MOLECULARLY IMPRINTED POLYMER AND A PROCESS FOR THE PREPARATION THEREOF

(75) Inventors: Börje Sellergren, Mainz (DE); Gunter Buchel, Frankfurt (DE)

(73) Assignee: MIP Technologies AB, Lund (SE)

( * ) Notice: Subject to any disclaimer, the term of this patent is extended or adjusted under 35 U.S.C. 154(b) by 484 days.

This patent is subject to a terminal disclaimer.

(21) Appl. No.: 11/051,508

(22) Filed: Feb. 7, 2005

(65) Prior Publication Data

US 2005/0189291 A1 Sep. 1, 2005

Related U.S. Application Data

(63) Continuation of application No. 10/111,816, filed as application No. PCT/SE00/02083 on Oct. 26, 2000, now Pat. No. 6,881,804.

(30) Foreign Application Priority Data

Nov. 2, 1999 (SE) .................................. 9903958

(51) Int. Cl.
C08F 12/02 (2006.01)
C08F 112/02 (2006.01)
(52) U.S. Cl. ....................... 526/346; 526/184; 526/319; 526/317.1
(58) Field of Classification Search ................. 526/184, 526/346, 319, 317.1
See application file for complete search history.

(56) References Cited

U.S. PATENT DOCUMENTS 5,786,428 A 7/1998 Arnold et al.

FOREIGN PATENT DOCUMENTS

| DE | 199 49 776 | 4/2001 |
| WO | WO 91/07349 | 5/1991 |
| WO | 95/21673 A1 | 8/1995 |
| WO | WO 95/21673 | 8/1995 |
| WO | WO 96/37527 | 11/1996 |

OTHER PUBLICATIONS

Johnson et al., Ordered Mesoprous Polymers of Tunable Pore Size from Colloidal Silica Templates, Science, 283, 963-965(1999).*
"Acrylic Polymer Preparations Containing Recognition Sites Obtained by Imprinting With Substrates", Olof Norrlöw et al., Journal of Chromatography, 299 (1984) Elsevier Science Publishers—pp. 29 to 41.
"Molecularly imprinted composite polymers based on trimethylolpropane trimethacrylate" (TRIM) particles for efficient enantiomeric separations, Magnus Glad et al., Reactive Polymers 25 (1995) Elsevier Science Publishers—pp. 47 to 54.

"Use of Silane Monomers for Molecular Imprinting and Enzyme Entrapment in Polysiloxane-Coated Porous Silica", Magnus Glad et al., Journal of Chromatography, 347 (1985) Elsevier Science Publishers—pp. 11 to 23.
"Imprint Coating: A Novel Synthesis of Selective Fuctionalized Ordered Mesoporous Sorbents", Sheng Dai et al., Communications, Angew. Chem. Int. Ed. 1999, 38, No. 9—pp. 1235 to 1239.
"The Use of Immobilized Templates—A New Approach in Molecular Imprinting", Ecevit Yitmaz et al., Communications, Angew. Chem. Int. Ed. 2000, 39, No. 12—pp. 2115 to 2118.
"Enzyme-Analogue Built Polymers, 18 Chiral Cavities in Polymer Layers Coated on Wide-Pore Silica", G,ünter Wulff et al., Reactive Polymers, 3 (1985) Elsevier Science Publishers—pp. 261 to 275.
"Molecular imprinting", Klaus Mosbach, Techniques, TIBS Jan. 19, 1994, Elsevier Science Publishers, pp. 9 to 14.
"Polymer Complements to Nucleotid Bases. Selective Binding of Adenine Derivatives to Imprinted Polymers", Kenneth J. Shea et al., J. Am. Chem. Soc. 1993, 115, pp. 3368 to 3369.
"Drug assay using antibody mimics made by molecular imprinting", George Vlatakis et al., Nature, vol. 361, Feb. 18, 1993, pp. 645 to 647.
"Highly Enantioselective and Substrate-Selective Polymers Obtained by Molecular Imprinting Utilizing Noncovalent Interactions. NMR and Chromatographic Studies on the Nature of Recognition", Börje Sellergren et al., J. Am. Chem. Soc. 1988, 110, pp. 5853 to 5860.
"Influence of polymer morphology on the ability of imprinted network polymers to resolve enantiomers", Börje Sellergren et al., Journal of Chromatography, 635 (1993) Elsevier Science Publishers—pp. 31 to 49.
"Molecular Imprinting of Amino Acid Derivatives at Low Temperature (0° C.) Using Photolytic Homolysis of Azobisnitriles", Daniel J. O'Shannessy, et al., Analytical Biochemistry 177, (1989) pp. 144 to 149.
"Separation of amino acids, peptides and proteins on molecularly imprinted stationary phases", Maria Kempe et al., Journal of Chromatography A, 691 (1995) Elsevier Science Publishers—pp. 317 to 323.
"Solid-phase Extraction of a Triazine Herbicide Using a Molecularly Imprinted Synthetic Receptor", Jun Matsul et al., Analytical Communications, Mar. 1997, vol. 34 pp. 85 to 87.

(Continued)

*Primary Examiner*—Ling-Sui Choi
(74) *Attorney, Agent, or Firm*—Buchanan Ingersoll & Rooney PC (57) ABSTRACT

A porous, molecularly imprinted polymer and a process for its preparation are described. The porous, molecularly imprinted polymer is characterized in that it is obtainable by providing a porous silica; attaching a molecular template to the surface of the porous silica; filling the pores of the porous silica with a polymer, removing the silica and the molecular template, thereby leaving a porous, molecularly imprinted polymer. The process is characterized by the above defined process steps. Also described are a porous polymer vesicle and its preparation with the same features as defined for the porous, molecularly imprinted polymer and its preparation, except for the lack of the molecular template and thus the lack of the molecular imprint in the porous polymer.

20 Claims, 2 Drawing Sheets

OTHER PUBLICATIONS

"Imprinted dispersion polymers: a new class of easily accessible affinity stationary phases", Börje Sellergren, Journal of Chromatography A, 673 (1994) Elsevier Science Publishers—pp. 133 to 141.

"Molecularly imprinted monodisperse microspheres for competitive radioassay", Lel Ye, et al., Anal. Commun., 1999, 36 pp. 35 to 38.

"Molecularly Imprinted Polymer Beads: Suspension Polymerization Using a Liquid Perfluorocarbon as the Dispersing Phase", Andrew G. Mayes et al., Analytical Chemistry, vol. 68, No. 21, Nov. 1, 1996—pp. 3769 to 3774.

"Surface Modification with Molecularly-Imprinted Polymers for Selective Recognition", Frances H. Arnold et al., 1991—pp. 97 to 98.

"Capillary Electrochromatography with Predetermined Selectivity Obtained through Molecular Imprinting", Leif Schweitz et al., Anal. Chem. 1997, 69, pp. 1179 to 1183.

"Comparison of polymer coatings of capillaries for capillary electrophoresis with respect to their applicability to molecular imprinting and electrochromatography", Oliver Brüggemann et al., Journal Chromatography A. 781 (1997) Elsevier Science Publishers—pp. 43 to 53.

"Enantioseparation of D,L-Phenylalanine by Molecularly Imprinted Polymer Particles Filled Capillary Electromatography", Jing-Ming Lin et al., J. Liq. Chrom. & Rel. Technol., 20(10), pp. 1489 to 1506 (1997).

"Molecularly imprinted polymers on silica: selective supports for high-performance ligand-exchange chromatography", Sean D. Plunkett et al., Journal of Chromatography A. 708 (1995) Elsevier Science Publishers—pp. 19 to 29.

"Ordered Mesoporous Polymers of Tunable Pore Size from Colloidal Silica Templates", Stacy A. Johnson et al., Science vol. 283, Feb. 12, 1999, pp. 963 to 965.

"Multiple Morphologies of "Crew-Cut"Aggregates of Polystyrene-b-poly(acrylic acid) Block Copolymers", Lifeng Zhang et al., Science vol. 268, Jun. 23, 1995—pp. 1728 to 1731.

"Self-Assembled Aggregates of Rod-Coil Block Copolymers and Their Solubilization and Encapsulation of Fullerenes", Samson A. Jenekhe et al., Science vol. 279, Mar. 20, 1998—pp. 1903 to 1907.

"Neuartige Polymerhohlkörper durch Selbstorganisation von Polyelektrolyten auf kolloidalen Templaten", Edwin Donath et al., Zuschriften, Angew. Chem. 1998, 110, pp. 2323 to 2327.

"A Realistic Diffusion Model for Ultrathin Polyelectrolyte Films", Regina V. Klitzing et al., Macromolecules 1996, 29 pp. 6901 to 6906.

"Ultrastable Mesostructured Silica Vesicles", Seong Su Kim et al., Science vol. 282, Nov. 13, 1998, pp. 1302 to 1305.

"Preparation of silica particles utilizing the sol-gel and the emulsion-gel processes", Ritva Lindberg et al., Colloids and Surfaces A: Physicochemical and Engineering Aspects 99 (1995) Elsevier Science Publishers—pp. 79 to 88.

"Production of Monodisperse Colloidal Silica Spheres: Effect of Temperature", Stöber et al., Journal of Colloid and Interface Science, vol. 118, No. 1, Jul. 1987—pp. 290 to 293.

Preparation of Porous Silica Spheres for Column Liquid Chromatography, Klaus Unger et al., Journal of Chromatography, 83 (1973) Elsevier Scientific Publishing Company, pp. 5 to 9.

"A Neutral Templating Route to Mesoporous Molecular Sieves", Peter T. Tanev et al., Science vol. 267, Feb. 10, 1995 pp. 865 to 867.

"A New Family of Mesoporous Molecular Sieves Prepared with Liquid Crystal Templates", J.S. Beck et al., J. Am. Chem. Soc. 1992, 114, pp. 10834 to 10843.

"Ordered mesoporous molecular sieves synthesized by a liquid-crystal template mechanism", C.T. Kresge et al., Nature vol. 359, Oct. 22, 1992—pp. 710 to 712.

"A Novel Pathway for Synthesis of Submicrometer-Size Solid Core/Mesoporous Shell Silica Spheres", Gunter Büchel et al., Communications, Adv. Mater. 1998, 10, No. 13—pp. 1036 to 1038.

Günter Wulff, *Molekulares Prägen (Imprinting) in Vernetzten Materialien Mit Hilfe Von Matrizenmolekülen—Auf Dem Weg Zu Künstlichen Antikörpern*, Angew. Chem., 1995, vol. 107, pp. 1958 to 1979.

Kenneth J. Shea, "*Molecular Imprinting of Synthetic Network Polymers: The De Novo Synthesis of Macromolecular Binding and Catalytic Sites*", TRIP, Polym. Sci., vol. 2, No. 5, May 1994, pp. 166 to 173.

Klaus Mosbach, "*Molecular Imprinting*", TIBS, Biochem. Sci., vol. 19, Jan. 1994, pp. 9 to 14.

Börje Sellergren, "*Enantiomer Separation Using Tailor-Made Phases Prepared by Molecular Imprinting*", A Practical Approach in Chiral Separations by Liquid Chromatography, G. Suhramrian, Ed., VCH, Weinheim, (1994), S., pp. 69 to 93.

Kenneth J. Shea et al., "*Polymer Complements to Nucleotide Bases. Selective Binding of Adenine Derivatives to Imprinted Polymers*", J. Am. Chem. Soc., vol. 115, 1993, pp. 3368 to 3369.

George Vlatakis et al., "*Drug Assay Using Antibody Mimics Made by Molecular Imprinting*", Nature, vol. 361, Feb. 18, 1993, pp. 645 to 647.

Börje Sellergren et al., "*Highly Enantioselective and Substrate-Selective Polymers Obtained by Molecular Imprinting Utilizing Noncovalent Interactions. NMR and Chromatographic Studies on the Nature of Recognition*", J. Am. Chem. Soc., vol. 110, 1988, pp. 5853 to 5860.

Börje Sellergren et al., "*Influence of Polymer Morphology on the Ability of Imprinted Network Polymers to Resolve Enantiomers*", Journal of Chromatography, vol. 635, 1993, pp. 31 to 49.

Daniel J. O'Shannessy et al., "*Molecular Imprinting of Amino Acid Derivatives at Low Temperature (0° C.) Using Photolytic Homolysis of Azobisnitriles*", Analytical Biochemistry, vol. 177, 1989, pp. 144 to 149.

Maria Kempe et al., "*Separation of Amino Acids, Peptides and Proteins on Molecularly Imprinted Stationary Phases*", Journal of Chromatography A, vol. 691, (1995), pp. 317 to 323.

Jun Matsui et al., "*Solid-Phase Extraction of a Triazine Herbicide Using a Molecularly Imprinted Synthetic Receptor*", Analytical Communications, Mar. 1997, vol. 34, pp. 85 to 87.

Börje Sellergren, "*Imprinted Dispersion Polymers: A New Class of Easily Accessible Affinity Stationary Phases*", Journal of Chromatography A, vol. 673, (1994), pp. 133 to 141.

Lei Ye et al., "*Molecularly Imprinted Monodisperse Microspheres for Competitive Radioassay*", Anal. Commun., 1999, vol. 36, pp. 35 to 38.

Günter Wulff et al., "*Enzyme-Analogue Built Polymers, 18 Chiral Cavities in Polymer Layers Coated on Wide-Pore Silica*", Reactive Polymers, Ion Exch., Sorbents, vol. 3, (1985), pp. 261 to 275.

Andrew G. Mayes et al., "*Molecularly Imprinted Polymer Beads: Suspension Polymerization Using a Liquid Perfluorocarbon as the Dispersion Phase*", Anal. Chem., 1996, vol. 68, No. 21, pp. 3769 to 3774.

Magnus Glad et al., "*Molecularly Imprinted Composite Polymers Based on Trimethylolpropane Trimethacrylate (TRIM) Particles for Efficient Enantiomeric Separations*", Reactive Polymers, vol. 25, (1995), pp. 47 to 54.

Frances H. Arnold et al., "*Surface Modification with Molecularly-Imprinted Polymers for Selective Recognition*", Polym. Prepr., vol. 36, No. 1., (1995), pp. 97 to 98.

Leif Schweitz et al., "*Capillary Electrochromatography with Predetermined Selectivity Obtained Through Molecular Imprinting*", Anal. Chem., 1997, vol. 69, pp. 1179 to 1183.

Oliver Brüggemann et al., "*Comparison of Polymer Coatings of Capillaries for Capillary Electrophoresis with Respect to their Applicability to Molecular Imprinting and Electrochromatography*", Journal of Chromatography A., vol. 781, (1997), pp. 43 to 53.

Jin-Ming Lin et al., "*Enantioseparation of D,L-Phenylalanine by Molecularly Imprinted Polymer Particles Filled Capillary Electrochromatography*", J. Liq. Chromatogr. Relat. Technol., vol. 20, (1997), pp. 1489 to 1506.

Sean D. Plunkett et al., "*Molecularly Imprinted Polymers on Silica: Selective Supports for High-Performance Ligand-Exchange Chromatography*", Journal of Chromatography A., vol. 708, (1995), pp. 19 to 29.

Stacy A. Johnson et al., "*Ordered Mesoporous Polymers of Tunable Pore Size From Colloidal Silica Templates*", Science, vol. 283, Feb. 12, 1999, pp. 963 to 965.

Lifeng Zhang et al., "*Multiple Morphologies of "Crew-Cut" Aggregates of Polystyrene-b-poly(acrylic acid) Block Copolymers*", Science, vol. 268, Jun. 23, 1995, pp. 1728 to 1731.

Samson A. Jenekhe et al., "*Self-Assembled Aggregates of Rod-Coil Block Copolymers and their Solubilization and Encapsulation of Fullerenes*", Science, vol. 279, Mar. 20, 1998, pp. 1903 to 1907.

Edwin Donath et al., "*Novel Hollow Polymer Shells by Colloid-Templated Assembly of Polyelectrolytes*", Angew. Chem. Int. Ed., vol. 37, No. 16, 1998, pp. 2201 to 2205.

Regine V. Klitzing et al., "*A Realistic Diffusion Model for Ultrathin Polyelectrolyte Films*", Macromolecules, vol. 29, 1996, pp. 6901 to 6906.

Gleb B. Sukhorukov et al., "*Hollow Polyelectrolyte Shells: Exclusion of Polymers and Donnan Equilibrium*", J. Phys. Chem. B., vol. 103, 1999, pp. 6434 to 6440.

Seong Su Kim et al., "*Ultrastable Mesostructured Silica Vesicles*", Science, vol. 282, Nov. 13, 1998, pp. 1302 to 1305.

Werner Stöber et al., "*Controlled Growth of Monodisperse Silica Spheres in the Micro Size Range*", Journal of Colloids and Interface Science, vol. 26, (1968), pp. 62 to 69.

Ritva Lindberg et al., "*Preparation of Silica Particles Utilizing the Sol-Gel and the Emulsion-Gel Processes*", Colloids and Surfaces A: Physicochemical and Engineering Aspects, vol. 99, (1995), pp. 79 to 88.

C.G. Tan et al., "*Production of Monodisperse Colloidal Silica Spheres: Effect of Temperature*", Journal of Colloid and Interface Science, vol. 118, No. 1, Jul. 1987, pp. 290 to 293.

Limin Qi et al., "*Micrometer-Sized Mesoporous Silica Spheres Grown Under Static Conditions*", Chem. Mater., vol. 10, 1998, pp. 1623 to 1626.

Klaus Unger et al., "*Preparation of Porous Silica Spheres for Column Liquid Chromatography*", Journal of Chromatography, vol. 83, (1973), pp. 5 to 9.

L. Chu et al., "*Microporous Silica Gels from Alkysilicate-Water Two Phase Hydrolysis*", Mater. Res. Soc. Symp. Proc., vol. 346, (1994), pp. 855 to 860.

Ch. Kaiser et al., "*Processing of Microporous/Mesoporous Submicron-Size Silica Spheres by Means of a Template-Supported Synthesis*", Characterisation of Porous Solids IV, Cambridge Royal Society of Chemistry, pp. 406 to 412.

Gunter Büchel et al., "*A Novel Pathway for Synthesis of Submicrometer-Size Solid Core/Mesoporous Shell Silica Spheres*", Advanced Materials, vol. 10, No. 13, 1998, pp. 1036 to 1038.

Peter T. Tanev et al., "*A Neutral Templating Route to Mesoporous Molecular Sieves*", Science, vol. 267, Feb. 10, 1995, pp. 865 to 867.

J.S. Beck et al., "*A New Family of Mesoporous Molecular Sieves Prepared with Liquid Crystal Templates*", J. Am. Chem. Soc., vol. 114, 1992, pp. 10834 to 10843.

C.T. Kresge et al., "*Ordered Mesoporous Molecular Sieves Synthesized by a Liquid-Crystal Template Mechanism*", Nature, vol. 359, Oct. 22, 1992, pp. 710 to 712.

Michael Grün et al., "*The Synthesis of Micrometer- and Submicrometer-Size Spheres of Ordered Mesoporous Oxide MCM-41*", Adv. Mater., vol. 9, No. 3, 1997, pp. 254 to 257.

Buchel, Gunter, et al.; "A Novel Pathway for Synthesis of Submicrometer-Size Solid Core/Mesoporous Shell Silica Spheres"; Advance Materials, 1998, pp. 1036-1038; No. 10; Wiley-VCH Verlag GmbH.

Ryoo, Ryong, et al.; "Synthesis of Highly Ordered Carbon Molecular Sieves via Template-Mediated Structural Transformation"; The Journal of Physical Chemistry B; Sep. 16, 1999; pp. 7743-7746; vol. 103, No. 37; American Chemical Society.

Johnson, Stacy A., et al.; "Ordered Mesoporous Polymers of Tunable Pore Size From Colloidal Silica Templates"; Science; Feb. 12, 1999; pp. 963-965; vol. 283.

* cited by examiner

POROUS, MOLECULARLY IMPRINTED POLYMER AND A PROCESS FOR THE PREPARATION THEREOF

This application is a continuation of application Ser. No. 10/111,816, filed Nov. 26, 2002 as a § 371 application of PCT/SE00/02083 with an international filing date of Oct. 26, 2000, which claims priority from Swedish application No. 9903958-8, filed Nov. 2, 1999.

FIELD OF THE INVENTION

Synthesis and use of porous network polymers and spherical polymer vesicles with molecular recognition properties by the use of mesoporous silica gel and core/shell silica gel particles as molecular pore- and cavity-templates.

The invention describes new nanostructured materials with selective binding properties for small molecules and biological macromolecules.

TECHNICAL BACKGROUND

In molecular imprinting in the presence of a template, polymers (MIPs) with high level of cross-linking are produced. The template corresponds regarding its structure and functionality to the target molecule [1, 2, 3, 4] and is after the synthesis removed, whereby cavities with forms and functionalities according to the template, remain. A number of imprinted polymers have until now been produced and the imprinting process constitutes a very promising way regarding the accomplishment of a large number of selective separations. The MIPs are distinguished by their high selectivity and affinity. In this way numerous materials with antibody like affinities can be produced. The advantages of the MIPs are their high association constants ($K_a$ up to $10^8$ $M^{-1}$) for the target molecule [5, 6] and their high stability. Disadvantages are the limited chromatographic separation capacity (broad and asymmetrical peaks at liquid-chromatography, LC), low load capacities (<3 mg/g), as well as a complicated preparation process with low yield. The low yield prevents a scaling up and the use of more expensive templates. Besides, there are only a few examples of successful imprinting of biological macromolecules.

(i) Production of Polymers with Molecular Recognition Properties (MIPs) as Monodispersed Particles.

Most of the MIPs are produced in the presence of a template through free radical polymerization of functional, unsaturated monomers (vinyl-, acryl- methacryl-) and an excess of di- or tri-unsaturated monomers (vinyl-, acryl-, methacryl-) as cross-linkers, where by porous, organic networks are produced. This method has the advantage that relatively stable polymers can be produced with the use of different solvents and at different temperatures [7], which is important in view of the different solubilities of the various templates.

Most of the non covalent molecular imprinting systems are based on acryl- or methacrylmonomers, as for instance methacrylic acid (MAA), which is cross-linked with ethylenegly-coldimethacrylate (EDMA). For the production of imprinted stationary phases for chiral separation (chiral stationary phases, CSPs) at the beginning derivates of amino acid enantiomers were used as templates. This system can generally be used for the imprinting of templates via hydrogen bonding or electrostatic interaction with MAA [8, 9]. The method is explicitly demonstrated by the example of L-Phenylalanina-nilid (L-PA).

In the first step the template (L-PA), the functional monomer (MAA) and the cross-linker (EDMA) are dissolved in a solvent with insignificant tendency towards forming hydrogen bonds and with small to average polarity. The free radical polymerization is thereafter started with an azo-initiator, for instance azo-N,N'-bis-isobutyronitril (AIBN), either photochemically at room temperature [11, 10] or thermochemically at 60° C. or higher [11]. The MIPs are formed as monoliths and before they are used they have to be crushed with mortar and pestle or with a ball mill. Following sieving the particles are sorted in the fractions 28-38 µm for chromatography resp. 150-200 µm for batch applications [11, 12, 13, 14, 15]. The template is extracted with a Soxhlet apparatus and thus recovered. The polymers as stationary phases are then evaluated by chromatography and the retention time and the capacity factors (k') [16] of the templates are compared with those of analog structures.

The work up of the polymers by crushing and sieving is associated with high costs and and a high loss of material in the form of fine particles. Besides it is difficult to produce these materials on a larger scale. By the sieving of the monolith particles irregular particles arise which not only have surface localized binding sites but also binding sites with poor accessibility. Due to flow disturbances and diffusion limitations this causes a poor separation performance in chromatography [17].

Therefore there is a need to produce MIP-materials in large quantities and with homogeneous morphology, as these regarding their mass transfer properties and their load capacity are superior compared to the irregular particles from the monolith method. Materials with homogenous morphology are already produced by bead polymerization [12, 18], dispersion polymerization [13] or precipitation polymerization [14]. The morphology of these products are very sensitive to small changes regarding the synthesis conditions and besides, only certain solvents can be used for the polymerization. By consequence the synthesis for each target template has to be optimized which is costly and clearly limits the use of this synthesis variant. In addition, the synthesis conditions for the production of spherical particles are not always compatible with those synthesis conditions which lead to a higher selectivity and affinity for the template molecules. An alternative is the coating of preformed support materials [15, 19, 20], through which MIPs can be produced on metallic oxides. [15, 20] Another is the coating of the MIPs on organic polymer supports [19] or on the walls of fused silica capillaries [21, 22, 23].

For instance, for the production of molecular imprinting polymer coatings, wide-pore silica gels (Silica 60, Silica 100, Silica 500 or Silica 1000 (Merck)), modified with 3-(Trimethoxysilyl)propyl-methacrylate and in connection treated with Hexamethyl-disilazanes (end-capping) have been used. The support is then coated with a thin layer (10-156 Å) of a monomer mixture (ethylenglycoldimethacrylat, EGDMA and meth-acrylic acid, MAA) in the presence of a chiral template and an initiator (azo-bis(isobutyronitril), AIBN). After polymerization (monomer grafting approach) [15], the resulting silica gels were sieved by wind sieving and thereafter sedimented and tested chromatographically. An other method consists in the coating of LiChrosphere 1000 with a metal complexing polymer layer. This is performed by coating of propylmethacrylat derivatized silica particles with a metal complexing polymer in presence of a metal coordinating template [24].

(ii) Use of Non Porous Silica Particles as Pore Template and Production of Polymer Vesicles The production of mesoporous polymers by use of colloidal silica particles as template was described by Johnson et al. [25]. Silica gel particles between 15 and 35 nm were settled and stabilized under pressure and heat. The spaces in the thus produced agglomerates of silica gel particles were then filled with a mixture of divinylbenzene (DVB) and an initiator (AIBN) and the polymerization started by heating to 60° C. The silica template was then dissolved with hydrofluoric acid or ammonium resp. cesium fluoride, whereby a vesical polymer frame was obtained, where the pore diameter can be varied through the dimension of the collodial silica gel.

Micro- and nanovesicles, which allows the inclusion of different materials, can be produced by spontaneous self-assembly of for instance amphiphilic block-copolymers [26, 27] or phosphorous lipids [28], by emulsion polymerization or by coating of colloidal particles with organic multilayered films. Thus it is possible to stepwise coat collodial melamin resin particles with polyelectrolyte molecules and subsequently dissolve the core [29]. The weakly cross linked melamine resin particles with density in the size range 0,1 to 10 μm serve as template, which can be dissolved at pH-values <1,6. The template is repeatedly coated with alternately charged polyelectrolytes. This coating is also stable after having dissolved the template, whereby polyelectrolyte vesicles are obtained whose dimensions are determined by the dimension of the template. The strength of the wall is determined in advance by the coating and can within wide limits be freely determined. In such a way polyelectrolyte vesicles can be produced, which show a selective permeability for polymers depending on their molecular weight. [30].

The selective permeability can for instance be used in order to create ionic conditions inside the vesicles which differ significantly from the volume phase [31].

By the use of neutral templates of type $C_nH_{2n+1}NH(CH_2)_2NH_2$ and tetraethoxysilane as silica source mesoporous molecular sieve with vesical structure can be obtained [32]. The vesicle is formed with one or more ca. 3-70 nm thick, wavy silica layers. The silica layers have mesopores in the size range 2,7-4,0 nm. The silica vesicles which are in the size range ca. 20 nm to 1400 nm, show a high thermal and hydrothermal stability.

(iii) Production of Non Porous Silica Gel Particles in the Range of Submicrometer and Micrometer The synthesis of non porous silica gel particles in the range of submicrometer and micrometer up to ca. 4 μm is based on works of Stöber et al. [33], whereby by hydrolysis and condensation of tetraalkoxysilanes in ammonia water and with ethanol as cosolvent monodisperse, spherical silica gel particles up to 1,6 μm, resp. polydisperse particles up to 3 μm are formed. The synthesis is exhaustively investigated in several reports [34, 35, 36]. The production of monodisperse silica gel particles up to 2,0 μm by hydrolysis and condensation of tetraethoxysilan at −20° C. [37] and the synthesis of spherical silica gel particles under acidic conditions have been described [38]. The synthesis of larger non porous silica gel particles up to 10 μm is performed in the two-phase system alkoxysilan/water, where, due to the ethanol formed during the reaction, the system is slowly transformed to one single phase. [39].

(iv) Synthesis of Monodisperse, Spherical, Porous Silica Gel Particles in the Submicrometer and Micrometer Range The production of porous silica gel particles in the range of micrometer (>5 μm) is performed by emulsion polymerization [40]. These exhibit a wide particle size range and have to be sieved. Porous silica gel particles in the nanometer range (<10 nm) have been described by Chu et al. [41]. The synthesis is based on a two-phase sol-gel process of silica without cosolvent.

Regarding the production of monodisperse, spherical, porous silica gel particles in the submicrometer range there is nothing known in the literature.

(v) Synthesis of Monodisperse, Spherical, Mesoporous Core/Shell Silica Gel Particles in the Submicrometer Range.

There is nothing known in the literature regarding synthesis of monodisperse, spherical silica gel particles with a non porous core and a mesoporous layer.

THE PRESENT INVENTION

The problem of poor site accessibility in molecularly imprinted polymers can in principle be solved through simultaneous use of porous and molecular templates as in this way a large number of molecular binding sites will be located on the surface. This procedure is called the double template method. In this invention we have developed a double template method which, through the use of porous silicagel, will make it possible to produce highly accessible molecularly imprinted binding sites in porous organic network polymers.

According to another aspect of the invention the use of core/shell particles with a porous shell and a nonporous core will make it possible to produce hollow vesicles with adjustable porosity. Combining the core/shell particles with the double template approach will allow the preparation of molecularly imprinted vesicles.

According to the present invention there is provided a porous, molecularly imprinted polymer, characterised in that it is obtainable by providing a porous silica;

attaching a molecular template to the surface of the porous silica;

filling the pores of the porous silica with one or several monomers followed by polymerisation of the monomers;

removing the silica and the molecular template, thereby leaving behind a porous, molecularly imprinted polymer.

The present invention also provides a process for the preparation of a molecularly imprinted polymer, characterised by providing a porous silica;

attaching a molecular template to the surface of the porous silica;

filling the pores of the porous silica with one or several monomers followed by polymerisation of the monomers;

removing the silica and the molecular template, thereby leaving behind a porous, molecularly imprinted polymer.

The present invention also provides a vesicle, characterised in that it is obtainable by providing silica particles with a nonporous core and a porous shell (core/shell particles);

filling the pores of the core/shell particles with one or several monomers followed by polymerisation of the monomers;

removing the silica, thereby leaving behind a porous, polymer vesicle.

The present invention also provides a process for the preparation of a vesicle, characterised by providing silica particles with a nonporous core and a porous shell (core/shell particles);

filling the pores of the core/shell particles with one or several monomers followed by polymerisation of the monomers;

removing the silica, thereby leaving behind a porous, polymer vesicle.

These and further characteristics and advantages of the present invention will become evident from the description given below and the apended claims.

According to the the first aspect of the invention a new class of molecular imprinted polymers are to be produced, at which the polymer morphology is controlled through the use of porous silica and the molecular recognition will be controlled through surface bound templates. The porous silicas act as porous templates and the surface linked molecules as template in order to acquire binding sites for molecules on the silica surface. The template, linked on the surface, is surrounded by a coating with a monomer mixture followed by the polymerization of the latter. Two model systems are illustrated schematically in FIGS. 1 and 2.

Figure 1:
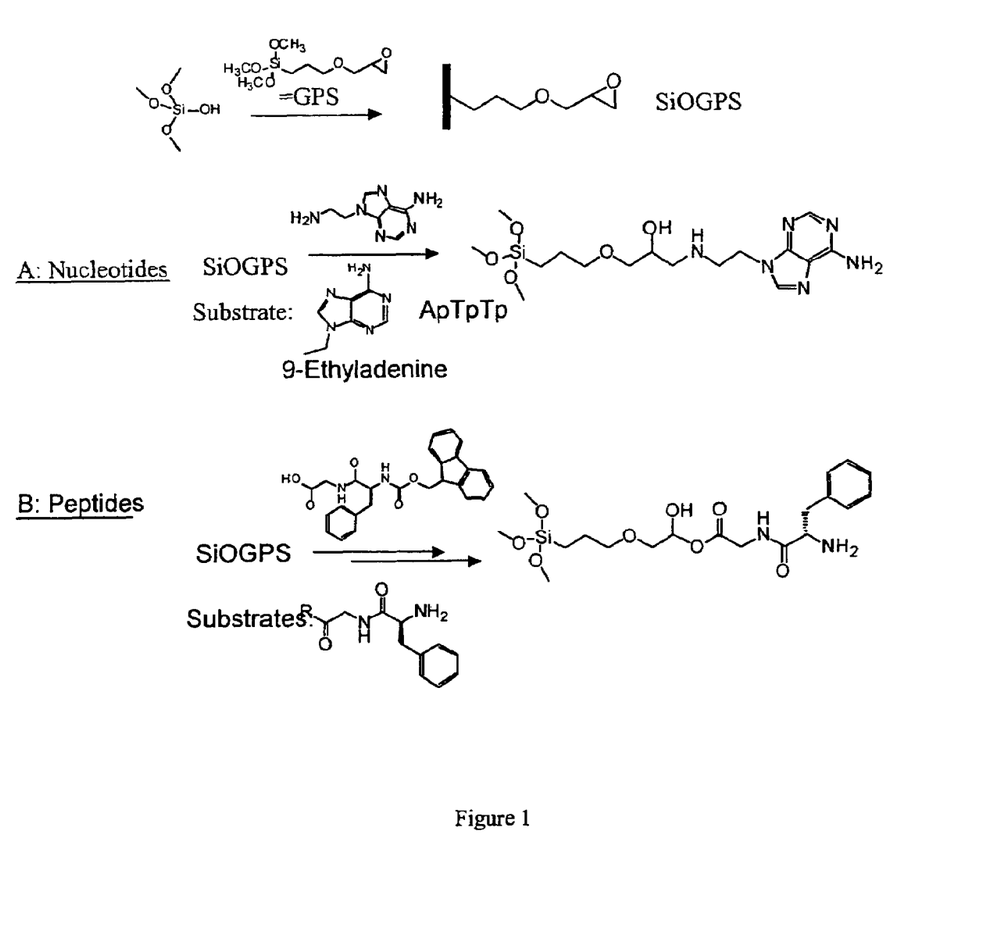
FIG. 1 schematically depicts a model system for the bonding of templates on the surface of silica gel and substrate for the test of the recognition of the corresponding templates.

In model system A nucleotide bases, oligonucleotides or derivatives thereof and in model system B aminoacid or peptide derivatives are bound to the surface through standard coupling chemistry. In FIG. 1 the silica surface is first silanised with glycidoxypropyltrimethoxy silane (GPS) to produce the corresponding epoxymodified silica surface (Si-OGPS). In model system A this surface is then reacted with a purine or pyrimidine base derivative such as 9-(2-aminoethyl) adenine). The pores of the silica particles are then filled with an appropriate monomer mixture, the monomers polymerised for instance by free radical polymerisation and then the silica template is dissolved out by treatment with fluoride, e.g. ammoniumfluoride. The binding sites resulting from the example in FIG. 1 would be complementary to 9-ethyl-adenine. Instead of modified silica, the template can also be made of controlled pore glass (CPG) which allows the direct use of the synthesis products resulting from solid phase DNA synthesis to be used as templates. Thus oligonucleotidemodified CPG can be used to create materials with affinity for the same oligonuclueotides, or DNA or RNA containing corresponding sequences.

In model system B the SiOGPS surface is instead reacted with aminoacid or peptide derivatives. Here the N-protected peptide FMOC-Phe-Gly is reacted with the epoxygroups on the surface. After deprotection pore filling with monomers, polymerisation and silica-dissolution are carried out as described above and the rusulting material can then be used to selectively bind corresponding peptides or corresponding N-terminal epitopes.

The model systems thus allow the production of surface located binding sites for nucleotide bases, oligonucleotides, amino acids or peptides at which, owing to the dissolution of the silicagel, spongy, macroporous materials are formed which can recognize the corresponding template. As the binding sites are localized on the surface of meso- or macroporous materials their accessibility are especially high due to short diffusion paths. In this way it is possible to strongly bind biological macromolecules, as for instance oligonucleotides, polypeptides or proteins, which contain epitopes corresponding to the template. The process is schematically shown once again in FIG. 2.

This process can be transferred to other silica gel morphologies, in order to produce porous polymer vesicles. This is done through the polymerization of a monomer mixture in the pores of porous core/shell silicagel particles. These silicagel particles consist of a non porous core and a porous shell. The morphology and the porosity of the polymer vesicle are further adjusted through variations of the core/shell silicagel synthesis. To this end the core/shell synthesis will be combined with different methods to produce porous silicagels. By the use of alkylsilanes, ionized or neutral pore creators and by variations of the conditions for the synthesis (temperature, concentration) the pore diameter of the shell as well as the particle size can be adjusted. After monomer filling, polymerisation and dissolution of the core/shell silica template, this will in turn allow vesicles with adjustable pore diameter to be prepared. Finally the synthesis of porous polymer vesicles can be combined with molecular imprinting.

The described methods make it possible to accomplish the double template method with a large number of different silica support materials of silica of different size and porosity. The use of porous silica supports as porous template combined with molecular imprinting for synthesis of surface imprinted particles with defined size and porosity is not known.

The research leading up to the present invention includes the following.

(i) MIPs with New Morphologies (a) Monolith Process

A model system for the production of MIPs according to the monolith process has been developed. To this end derivatives of amino acid enantiomers, for instance (e.g. L-phenylalanineanilid (L-PA) and the nucleotidebase derivative (9-Ethyladenin) were used as template. These interact via hydrogen bonding and electrostatic interactions with the functional monomer (MAA). For the photochemical polymerization at room temperature AIBN was used as initiator. After crushing and sieving of the polymers and after extraction of the template the material was evaluated in chromathography regarding its selectivity for the template. It functions as model system with which materials obtained according to the double template principle have to be be compared.

(b) Polymer Coating of Spherical Silica Supports

For the production of spherical molecularly imprinted particles non porous, spherical silica gel (particle diameter: 1-5 µm) and porous, spherical silica gel (particle diameter: 10 µm, pore diameter: 1000 Å) are used. These were coated with the MIPs according to two different methods of which one, according to Wulff et al., consisted of modification of the surface with 3-(trimethoxysily)propylmethacrylate followed by reaction of remaining silanol groups (endcapping). After that the silica gel was coated with the monomer mixture (MAA, EDMA) containing the template (L-PA) and the initiator (AIBN) the polymerization was photochemically started.

A further way to coat the silica gels with MIPs is possible by a technique based on a method described by Guyot et al. In this case the silica surface was first silanized with 3-aminopropyltriethoxysilane or glycidoxypropylsilane (GPS). Subsequently the amino resp. epoxy group were reacted with the initiator (Azo-bis(cyanopentanoic acid, ACPA). After coating with the monomer mixture the polymerization was photochemically carried out where the particles were suspended in the monomer mixture.

(ii) Synthesis of Porous, Spherical Silica Gel Particles using Different Pore Creators (a) Alkyltrialkoxysilane (Octadecyltrimethoxysilane, C18-TMS) as Pore Creator By cohydrolysis and cocondensation of tetraethoxysilane (TEOS) and octadecyltrimethoxysilane as reactive silane in ammonia water and with ethanol as cosolvent spherical organo silica gel composites are created. These composites can be transformed into mesoporous, spherical silica gel particles by calcination at 550° C. The material shows a specific surface $a_s$ (BET) up to 750 m$^2$/g, a specific pore volume (Gurwitsch) up to 0.6 mL/g and an average pore diameter, according to synthesis conditions, between 2 nm and 4 nm. By variation of the reaction temperature and the concentration of water resp. ammonia the particle size can be regulated up to 900 nm [42, 43, 44, 45].

(b) Neutral Templates (Alkylamines) as Pore Creators

The use of n-alkylamines for the synthesis of mesoporous metal oxides was first tried by T. J. Pinnavaia [46]. These products showed an irregular morphology. By changing to a homogenous reaction system through the use of alcohol as cosolvent, the use of ammonia as catalyst and by variation of the concentration of the template and the silica-precursor it has been possible to obtain mesopouros and spherical SMS-materials (spherical mesoporous amine-templated silica) [47]. These particles have a diameter of up to 2 μm and show a specific surface, $a_s$ (BET), up to 800 m$^2$/g, a specific pore volume (Gurwitsch) up to 0,8 mL/g and an average pore diamater (Wheeler) of 3,0.

(c) Ionic Tensides (n-Alkyltrimethylammoniumbromide) as Template

The synthesis of mesoporous metal oxides of the M41S class and their use as cracking catalyst for the petrochemical application dates back to works by scientist at the Mobil Oil Corporation from the year 1992 and back [48, 49]. This is exemplified by the highly porous MCM-41 with its hexagonal arranged, cylindrical pore system. Through the synthesis of these materials in a single-phase system, i.e. through the use of tetraethoxysilane as silica source, alcohol as cosolvent and aqueous ammonia as catalyst, it has been possible to produce spherical particles with MCM-41-analog structure [48, 49, 50]. These materials have, each according to length of alkylchain and concentration of the templates a specific surface, $a_s$ (BET), up to 1300 m$^2$/g, a specific pore volume (Gurwitsch) up to 0,8 mL/g and a pore diameter (Wheeler) of ca. 2,0 nm.

(d) Polymers (Polyethylenoxide) as Pore Creators

For synthesis of spherical silica gel particles with pore diameter up to 50 nm polyethylenoxide (PEO) dissolved in a mixture of water, alcohol and ammonia is used. By adding TEOS, ca. 200 nm large, spherical silica gel composites are produced, which after filtration, drying and calcination have got a specific surface $a_s$ (BET) up to 550 m$^2$/g and a specific pore volume up to 0,9 mL/g [51].

(iii) Synthesis of Mesoporous Core/Shell Silica Gel Particles

The synthesis of mesoporous core/shell silica gel particles depends on the combination of three known methods: at first the non porous silica gel core is produced according to the well-known Stöber-method [33-36]. The size can be adjusted between 100 nm and 3,0 μm by variations of the reaction temperature, the concentration of the water and the ammonia and by variation of the kind and concentration of the alkoxysilane and the alcohol. The following synthesis of the porous layer is based upon a combination of two well-known synthesis methods: on the one hand the synthesis of porous silica gel particles through cohydrolysis and cocondensation of tetraethoxysilane and C18-TMS [42-45], the method of the post growth on the other hand was originally developped for the enlargement of non porous silica gel particles. [52]. In this way it was possible by adding tetraethoxysilane drop by drop to a suspension of spherical, non porous silica gel particles in water, ethanol and ammonia, to increase the particle size from originally 500 nm to 3 μm. For the synthesis of the core/shell silica gel particles, a mixture of TEOS/C18-TMS, without any further processing, is dropped directly into the reaction suspension of the non porous Stöberparticles. The porosity is obtained by a following calcination at 550° C. [45, 53, 54].

By varying the quantity of added pore creator it is possible to produce mesoporous core/shell silica gel particles with a specific surface $a_s$ (BET) of up to 350 m$^2$/g, a specific pore volume $v_p$ (Gurwitsch) up to 0,4 ml/g and an average pore diameter $p_d$ (BJH, des.) of 3,8 nm.

Particular Embodiments of the Invention (i) Accomplishment of the Double Template Principle using Porous Silica Supports The techniques used to coat polymers on non porous or macroporous silica gels shall be extended to pore filling of porous silica supports. Thereby serves a porous silica gel as morphological template and a surface bound template molecule as molecular template.

Porous silica will be used as spherical silica gels. Pore systems of different size and structure are then available through the different techniques to prepare porous spherical silica gels. Then the molecular template, as described in FIG. 1, is bound to the silica surface. Two model systems are available, at which in the first a peptide and in the second a nucleotide are fixed on the surface. Then the pore system of the porous, template modified silica gel is, evacuated and filled with a monomer mixture followed by a polymerization, according to the process of Mallouk. [25]

Thereafter the silica gel is dissolved using hydrofluoric acid or calcium or ammonium fluoride, whereby a porous, spherical polymer with binding sites localized on the surface is obtained.

Figure 2:
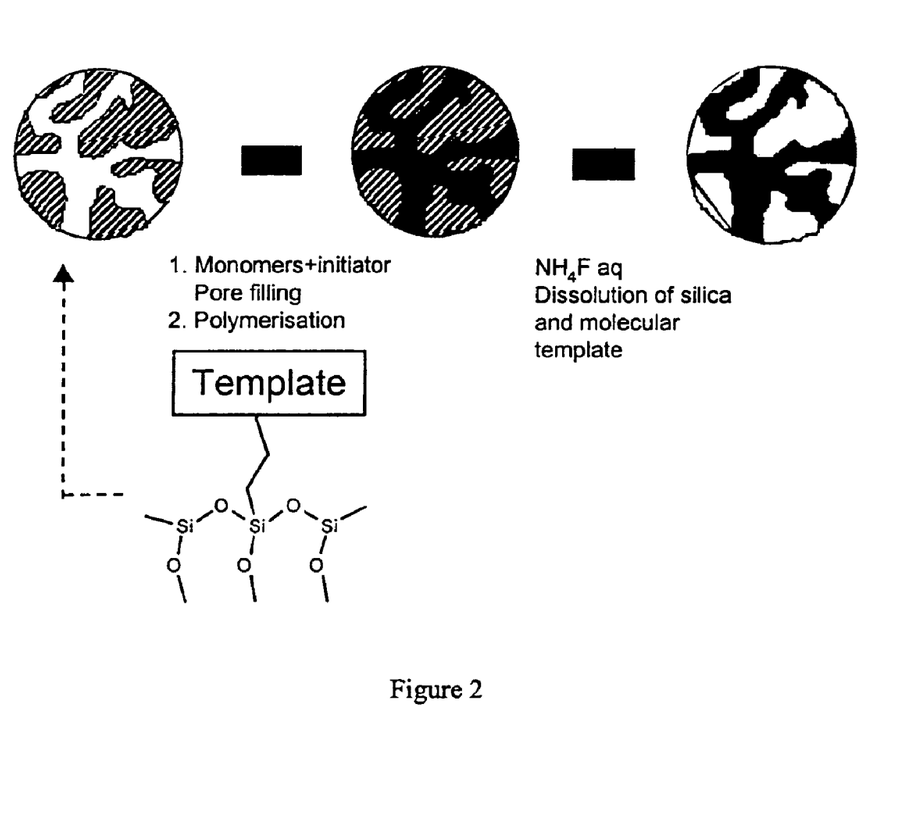
FIG. 2 schematically depicts the use of porous silica gel particles as pore template in molecular imprinting.

The polymerization of the monomer mixture can take place in the pores of mesoporous, template-modified silica gels (FIGS. 1 and 2). Hereby serves a number of different porous silica gel materials as support materials. For example spherical silica gels with a cylindrical pore system (M41S Class) can be used herefor, silica gels, which are composed of a nanoparticle agglomerate (SMS-Class resp. n-Alkyltrialkoxysilane as pore creators) or silica gels with polymers as pore creators. In this way different pore systems with regard to their size and structure are available. The silica surface is then to be silanisized with for instance glycidoxypropylsilane (GPS) and in connection reacted with the aminogroup of the templates (9-(2-aminoethyl)adenine), model system I) or the carboxyl group of the templates (FMOC-L-Phe-L-Gly, model system II).

Instead of modified silica, the template can also be made of controlled pore glass (CPG) which allows the direct use of the synthesis products resulting from solid phase DNA synthesis to be used as templates. Thus oligonucleotidemodified CPG can be used to create materials with affinity for the same oligonuclueotides, or DNA or RNA containing corresponding sequences.

After removing of the solvent and evacuation of the silica or CPG pore system this is filled with the monomer mixture (MAA, EDMA) and the polymerization is photochemically started using AIBN. Then the silica gel is dissolved out with hydrofluoric acid or calcium or ammonium fluoride, by which a porous, spherical spongy polymer with affinity to the target molecule is obtained.

(ii) Production of Micro- and Nanovesicles using Mesoporous Core/Shell Silica Gel Particles The under (i) described method for porefilling of porous silica gels can be used for filling the pores of porous core/shell silica gels, i.e. silica gels with a non porous core and a porous shell. After polymerisation of the monomer mixture and dissolving the silica core with hydrofluoric acid or fluorides a porous polymer vesicle remains.

The size and porosity of the mesoporous core/shell silica gel particles can be further adjusted to requirements for chromatographic materials, whereby a particle diameter of over 2 μm is the objective. This is made by adjustment of the synthesis conditions for the core/shell silica gel particle. Through different methods regarding the synthesis of porous, spherical silica gel particles, support materials of different size, pore diameter and pore symmetri are available. By the thickness of the porous layer the specific surface area and the stability of the thus resulting polymer vesicle can then also be increased.

The process for coating of porous silica gels described in step (i) can be transferred to the coating of porous core/shell materials. Thus the template (L-Phe-L-Gly or a nucleotide base) can directly react with the GPS-silanisized silica surface (FIG. 1). After that the pore system is filled with the monomer mixture (MAA, EDMA) and the polymerization is performed with AIBN as initiator. By dissolving out the silica core, for instance with hydrofluoric acid or ammonium fluoride, porous polymer vesicles are formed, the size and porosity of which is decided through the porous properties of the corresponding core/shell particle. The mechanical stability can be by increasing the polymer thickness, i.e. as a result of the size of the porous layer of the core/shell particle and the pore diameter can be adjusted through the pore diameter of the core/shell particle. By drop by drop addition of TEOS/C18-TMS mixture and by dilution of the silica gel suspension during the after growth process, agglomeration can be prevented also at larger quantities of added silane mixture [55]. The porous core/shell silica gel particles can be be adapted regarding their size and porosity according to the requirements on the resulting micro vesicles. Hereby the aim is to obtain spherical particles with a diameter of more than 2 μm, as otherwise in the HPLC, the pressure in the chromatographic column will be too high. This can be obtained by enlargement of the non porous silica core. The core particle size can be raised by variation of the reaction temperature, the solvent, the ammonia concentration and the alkoxysilane source. In this way the non porous silica core can be enlarged by up to 3,0 μm. References to this are to be found in the literature. Further on spherical silica gel particles up to 10 μm are obtainable by synthesis in two-phase systems [41].

By combination with the already known process for the production of mesoporous silica gel particles, the porosity can be varied within the total mesoporous area, i.e. between 2 and 50 nm. For this purpose ionic (n-alkyltrimetylamminiumbromide) and non ionic template (n-alkylamine) and polymers (polyethylenoxide) are suited. These processes are all based on the hydrolysis and condensation of tetraalkoxysilanes in the presence of a pore creator in ethanol solution with ammonia as catalyst. It can then be combined with the already known methods for synthesis of core/shell silica gel particles.

The use of the porous core/shell silica gel particles provides the advantage of the flexible adjustment of specific surface and pore diameter. In this way the size of the polymer vesicle and the porosity and thickness of the vesicle wall can be carefully tuned.

(iii) Production of Porous Micro- and Nanovesicles with Molecular Recognition Properties The process can be extended to vesicles with molecular recognition properties. For this purpose, a template (see FIG. 1) is required, which is bound to the particle surface or added as a mixture with the monomer. After the following polymerization and after the extraction of the template the core will be dissolved and thus a porous polymer vesicle will be formed, exhibiting a pronounced affinity for the template.

To this end either the template 9-(2-aminoethyl)-adenine, (model system I) or FMOC-L-Phe-L-Gly, (model system II) can be used. These react with the epoxygroups of the silica surface bound GPS. After processing of the products the pores are filled with the monomer mixture and the initiator (AIBN) and polymerized. After the following polymerization the template and the silica core are dissolved leaving behind a spherical, porous polymer vesicle which shows a high affinity to the target molecule.

(iv) The use of Spherical Molecularly Imprinted Particles and Porous Core/Shell Silica Gel Particles The spherical MIPs and the spherical polymer vesicles can be compared chromatographically regarding their selectivity and load capacity with the through the monolithprocess produced reference material. For this purpose, liquid chromatography (LC) or high performance liquid chromatography (HPLC) will be used according to stability of the materials. The porous polymer vesicles can further be used for storing, protection and target oriented liberation of drugs (Slow Release System).

Beside the use in chromatography, the porous core/shell silica gel particles may, after entrapment of metals, constitute potential support materials for catalytic applications.

The obtained porous, spherical polymers and the porous polymer vesicles are tested chromatographically (LC bzw. HPLC) regarding their selectivity and compared with the materials from the monolith process.

For the porous polymer vesicles there are, beside chromatography, a wide field of applications. Vesicles can be prepared by controlled coating with several polymer layers on the silica surface. Such vesicles can for instance on the inside wall particularly contain amino groups, and on the outside wall on the contrary carboxyl or sulphonate groups. Furthermore, vesicles with amphiphilic groups in the interior of the capsules and hydrophilic groups on the outer wall can also be produced. By successive exchange of the aqueous solvent interior of the vesicles with an oil stable oil/water emulsions can be produced.

The porous polymer vesicles can further be used for storing and target oriented liberation of drugs (Slow Release System). The vesicle membrane exhibits due to its porosity and its chemical structure, a selective permeability which can be adjusted depending on planned application. The selective permeability of the vesicle walls can be used for instance via the setting of a Donann-partitioning in the interior of the capsules resulting in ionic conditions, which are different from the volume phase. Thus can for instance, due to different pH values in the interior of the vesicles and in the volume phase, selective chemical reactions inside the vesicle be carried out.

The porous core/shell silica gel particles have a high specific surface, which is concentrated within a thin shell on the surface of spherical silica gels. By silanization, reverse phase silica gel materials can be produced, which because of faster mass transport inside the silica gel particle should show distinct improvments compared to existing chromatographic stationary phases.

Besides the use in the chromatography the porous core/shell silica gel particles can, after doping with metals (Ni, Mo, Pt, etc.), function as potential support materials for catalytic applications. In addition the core/shell silica gel particles show a higher thermal and hydrothermal stability than common mesoporous silica gel materials [48], which is important for catalytic applications.

[1] G. Wulff, *Angew. Chem.*, 107 (1995) 1958
[2] K. J. Shea, *Tr. Polym. Sci.*, (1994) 2
[3] Mosbach, K., *Tr. Biochem. Sci.*, 19 (1994) 9
[4] B. Sellergren, in: A practical approach to chiral separations by liquid chromatography. G. Subramanian, Ed., VCH, Weinheim (1994), S. 69
[5] K. J. Shea, D. A. Spivak, B. Sellergren, *J. Am. Chem. Soc.*, 115 (1993) 3368.
[6] G. Vlatakis, L. I. Andersson, R. Müller, K. Mosbach, *Nature*, 361 (1993) 645.
[7] J. M. G. Cowie, *Polymers: Chemistry & Physics of modern materials*. Glasgow: Blackie and Son Ltd. (1991)
[8] B. Sellergren, M. Lepistoe, K. Mosbach, *J. Am. Chem. Soc.*, 110 (1988) 5853
[9] B. Sellergren, K. J. Shea, *J. Chromatogr.*, 635 (1993) 31
[10] D. J. O'Shannessy, B. Ekberg, K. Mosbach, *Anal. Biochem.*, 177 (1989) 144
[11] M. Kempe, K. Mosbach, *J. Chromatogr.* 1995
[12] J. Matsui, M. Okada, M. Tsuruoka, T. Takeuchi, *Anal. Commun.*, 34 (1997) 85
[13] B. Sellergren, *J. Chromatogr. A*, 673 (1994) 133
[14] Y. Lei, P. A. G. Cormack, K. Mosbach, *Anal. Commun.* 36 (1999) 35
[15] G. Wulff, D. Oberkobusch, M. Minarik, *React. Polym., Ion Exch., Sorbents.*, 3 (1985) 261
[16] L. R. Snyder, J. J. Kirkland, *Introduction to Modern Liquid Chromatography*. US: Wiley (1979)
[17] K. K. Unger, E. Weber, Eds., Handbuch der HPLC, Git Verlag, Darmstadt (1995)
[18] A. G. Mayes, K. Mosbach, *Anal. Chem.* 68 (1996) 3769
[19] M. Glad, P. Reinholdsson, K. Mosbach, 1995. *React. Polym.* 25 (1995) 47-54
[20] F. H. Arnold, S. Plunkett, P. K. Dhal, S. Vidyasankar, *Polym. Prepr.* 36(1) (1995) 97
[21] L. Schweitz, L. I. Andersson, S. Nilsson, *Anal. Chem.* 69 (1997) 1179
[22] O. Brüggemann, R. Freitag, M. J. Whitcombe, E. N. Vulfson, E. N., *J. Chromatogr.* 781 (1997) 43
[23] J.-M. Lin, T. Nakagama, K. Uchiyama, T. Hobo, T., *J. Liq. Chromatogr. Relat Technol.* 20 (1997) 1489
[24] S. D. Plunkett, F. Arnold, *J. Chromatogr.*, 708 (1995) 19
[25] S. Johnson, P. Ollivier, T. Mallouk, *Science*, 283 (1999) 96
[26] L. Zhang, A. Eisenberg, *Science*, 268 (1995) 1728
[27] S. A. Jehnke, X. L. Chen, *Science*, 279 (1998) 1903
[28] D. D. Lusic, Liposomes: From Physics to Application, Elsevier, Amsterdam (1993)
[29] E. Donath, G. B. Sukhorukov, F. Caruso, S. A. Davies, H. Möhwald, *Angew. Chem.*, 110 (1998) 2324
[30] R. von Klitzing, H. Möhwald, *Macromolecules*, 29 (1996) 6901
[31] G. B. Sukhorukoc, M. Brumen, E. Donath, H. Möhwald, J. Phys. Chem. B, eingereicht
[32] S. S Kim, W. Zhang, T. Pinnavaia, *Science*, 282 (1998) 1302
[33] W. Stöber, A. Fink, E. Bohn, *J. Colloid Interface Sci.*, 26 (1968) 62
[34] R. Lindberg, J. Sjöblom, G. Sundholm, *Colloids Surfaces A: Physiochem. Eng. Aspects*, 99 (1995) 79
[35] R. K. Iler, The Chemistry of Silica, Wiley, New York (1979)
[36] C. J. Brinker, G. W. Scherer, Sol-Gel-Science, Academic Press (1990)
[37] C. G. Tan, B. D. Bowen, N. Epstein, *J. Colloid Interface Sci.*, 118 (1987) 290
[38] L. Qi, J. Ma, H. Cheng and Z. Zhao, *Chem. Mater.*, 10 (1998) 1623
[39] T. Barder, P. David, Int. Patent Applikation PCT/US90/03605
[40] K. K. Unger, J. Schick-Kalb and K.-F. Krebs, *J. Chromatogr.*, 83 (1973) 5
[41] L. Chu, M. I. Tejedor-Tejedor, M. A. Anderson, *Mater. Res. Soc. Symp. Proc.*, 346 (1994) 855
[42] C. Kaiser, Dissertation, Johannes Gutenberg-Universität Mainz (1996)
[43] Ch. Kaiser, G. Büchel, S. Lüdtke, I. Lauer, K. K. Unger, Processing of microporous/mesoporous submicron-size silica spheres by means of a template-supported synthesis in: Characterisation of Porous Solids IV, B. McEnaney, T. J. Mays, J. Rouquérol, F. Rodriguez-Reinoso. K. S. W Sing and K. K. Unger, Eds. Cambridge: Royal Society of Chemistry
[44] G. Büchel, M. Grün, K. K. Unger, A. Matsumoto and K. Tsutsumi, *Supramolecular Science*, 5 (1998) 253
[45] G. Büchel, Dissertation, Johannes Gutenberg-Universität Mainz (1999)
[46] P. T. Tannev, T. J. Pinnavaia, Science, 267 (1995) 865
[47] M. Grün, Dissertation, Johannes Gutenberg-Univeität Mainz (1999)
[48] J. S. Beck, W. J. Roth, M. E. Leonowicz, C. T. Kresge, K. K. Schmitt, C. T. W. Chu, D. H. Olson, E. W. Sheppard, S. B. McCullen, J. B. Higgins, J. L. Schlenker, J. Am. Chem. Soc., 114 (1992) 10834
[49] C. T. Kresge, M. E. Leonowicz, W. J. Roth, J. Vartuli, J. S. Beck, Nature, 359 (1992) 710
[50] M. Grün, I. Lauer, K. K. Unger, Adv. Mater., 9 (1997) 254
[51] K. Schumacher, S. Renker, Institut für Mikrotechnik Mainz, K. K. Unger, zum Patent angemeldet
[52] H. Giesche, Dissertation, Johannes Gutenberg-Universität Mainz (1987)
[53] G. Büchel, K. K. Unger, A. Matsumoto, K. Tsutsumi, *Adv. Mater.*, 10 (1998) 1036
[54] G. Büchel, K. K. Unger, A. Matsumoto, K. Tsutsumi, Synthesis of Submicron Size Solid Core/Mesoporous Shell Silica Spheres, Proceedings to Silica'98 Symposium, Sept. 1-4, Mulhouse, France, 509-512

The invention claimed is:

1. A porous, molecularly imprinted polymer to act as a receptor for a specific target molecule, wherein said porous, molecularly imprinted polymer is produced by a process of:
   providing a porous solid support;
   attaching a molecular template to the surface of the porous solid support, wherein said molecular template is selected to correspond in structure and functionality to a target molecule;
   filling the pores of the porous solid support with one or several monomers followed by polymerization of the monomers; and
   removing the solid support and the molecular template, thereby leaving behind a porous molecularly imprinted polymer.

2. A porous, molecularly imprinted polymer according to claim 1, wherein the porous solid support is silica.

3. A porous, molecularly imprinted polymer according to claim 2, wherein the polymer is comprised of porous particles.

4. A porous, molecularly imprinted polymer according to claim 3, wherein the particles are spherical particles.

5. A porous, molecularly imprinted polymer according to claim 3, wherein the polymer is comprised of vesicular particles.

6. A porous, molecularly imprinted polymer according to claim 3, wherein the particles have an average particle size of at least 2 micrometer.

7. A porous, molecularly imprinted polymer according to claim 6, wherein the particles have an average particle size of 2-10 micrometer.

8. A porous, molecularly imprinted polymer to act as a receptor for a specific target molecule, wherein said porous, molecularly imprinted polymer is produced by a process of:
  providing a porous solid support;
  attaching a molecular template to the surface of the porous solid support, wherein said molecular template is selected from an epitope of an oligonucleotide, a polypeptide, or a protein;
  filling the pores of the porous solid support with one or several monomers followed by polymerization of the monomers; and
  removing the solid support and the molecular template, thereby leaving behind a porous molecularly imprinted polymer.

9. A process for the preparation of a molecularly imprinted polymer comprising
  providing a porous solid support; attaching a molecular template to the surface of the porous solid support;
  filling the pores of the porous solid support with one or several monomers followed by polymerization of the monomers;
  removing the solid support and the molecular template, thereby leaving behind a porous, molecularly imprinted polymer.

10. A process according to claim 9, wherein the porous solid support comprises silica.

11. A process according to claim 10, wherein the porous silica comprises particles.

12. A process according to claim 11, wherein the particles are spherical particles.

13. A process according to claim 10, wherein the particles are of a core/shell type having a non-porous core of silica surrounded by porous silica.

14. A process according to claim 10, wherein the porous silica is mesoporous.

15. A process according to claim 14, wherein the porous silica has a pore size of 2-50 nanometer.

16. A process according to claim 10, wherein the porous silica particles have a particle size of at least 2 micrometer.

17. A process according to claim 10, wherein the molecular template is covalently attached to the surface of the porous silica.

18. A process according to claim 10, wherein the pores of the porous silica are filled with the polymer by introducing at least one monomer into the pore and polymerizing it into a polymer.

19. A process according to claim 10, wherein the porous silica and the molecular template are removed by dissolution with a solvent.

20. A process according to claim 19, wherein the solvent is selected from hydrofluoric acid, calcium fluoride, and ammonium fluoride.

* * * * *